(12) United States Patent
Watanabe

(10) Patent No.: US 8,160,207 B2
(45) Date of Patent: Apr. 17, 2012

(54) RADIATION IMAGING APPARATUS

(75) Inventor: Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 211 days.

(21) Appl. No.: 12/725,544

(22) Filed: Mar. 17, 2010

(65) Prior Publication Data

US 2010/0254517 A1    Oct. 7, 2010

(30) Foreign Application Priority Data

Apr. 2, 2009 (JP) ................. 2009-090486

(51) Int. Cl.
*G21K 1/00* (2006.01)
(52) U.S. Cl. .......................... 378/154; 378/189
(58) Field of Classification Search .......... 378/62, 378/98.8, 145, 147–149, 154, 189
See application file for complete search history.

(56) References Cited

U.S. PATENT DOCUMENTS

| 7,019,300 B2 | 3/2006 | Watanabe ................. 250/370.08 |
| 7,104,686 B2 | 9/2006 | Watanabe et al. ............. 378/189 |
| 7,180,073 B2 | 2/2007 | Tetsuo ...................... 250/370.08 |
| 2009/0010394 A1 | 1/2009 | Watanabe ..................... 378/145 |

FOREIGN PATENT DOCUMENTS

JP    2004-177251    6/2004

*Primary Examiner* — Courtney Thomas
(74) *Attorney, Agent, or Firm* — Fitzpatrick, Cella, Harper & Scinto

(57) ABSTRACT

A radiation imaging apparatus comprising a detection unit for detecting a radiation distribution transmitted through an object, an imaging unit which includes the detection unit, and a grid for suppressing scattered light which is detachably mounted on an outside of the imaging unit, wherein the imaging unit includes a buffer member on a side surface facing a surface side which radiation strikes, the grid includes a grid body placed on the surface side which the radiation strikes, and a fixing unit for fixing the grid body to the imaging unit, and sides constituting the fixing unit include a side which does not protrude from an outer shape of the imaging unit when viewed from the surface side which the radiation strikes.

6 Claims, 5 Drawing Sheets

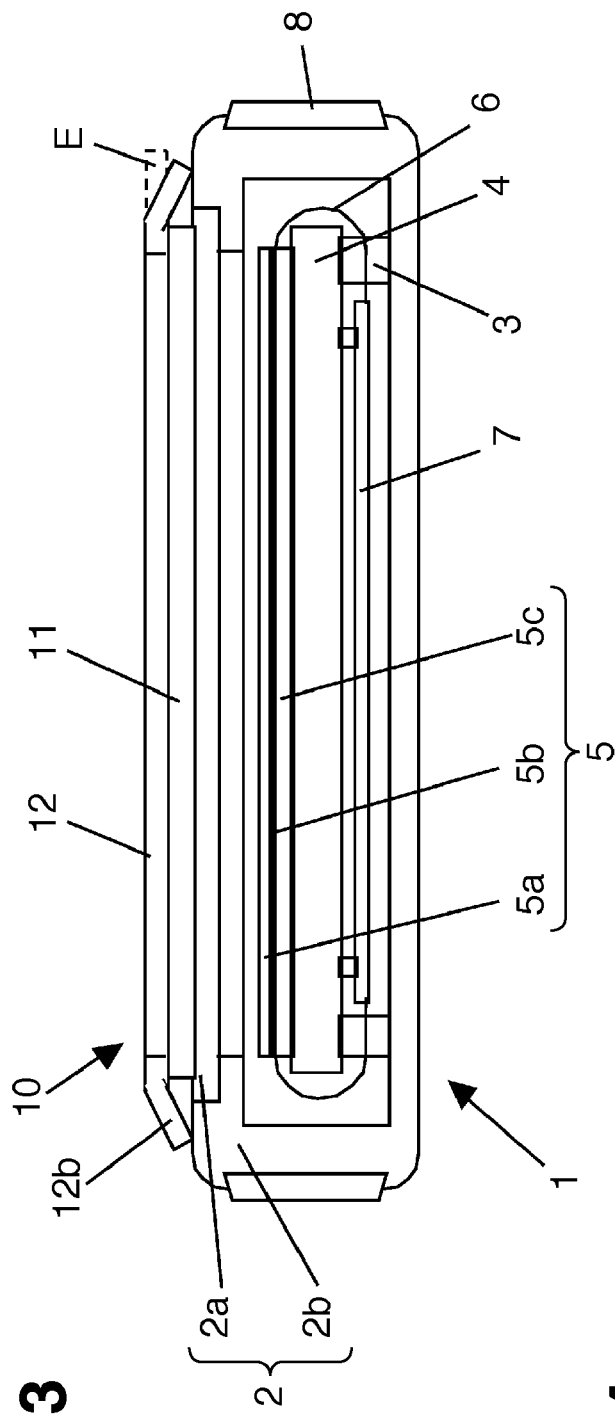
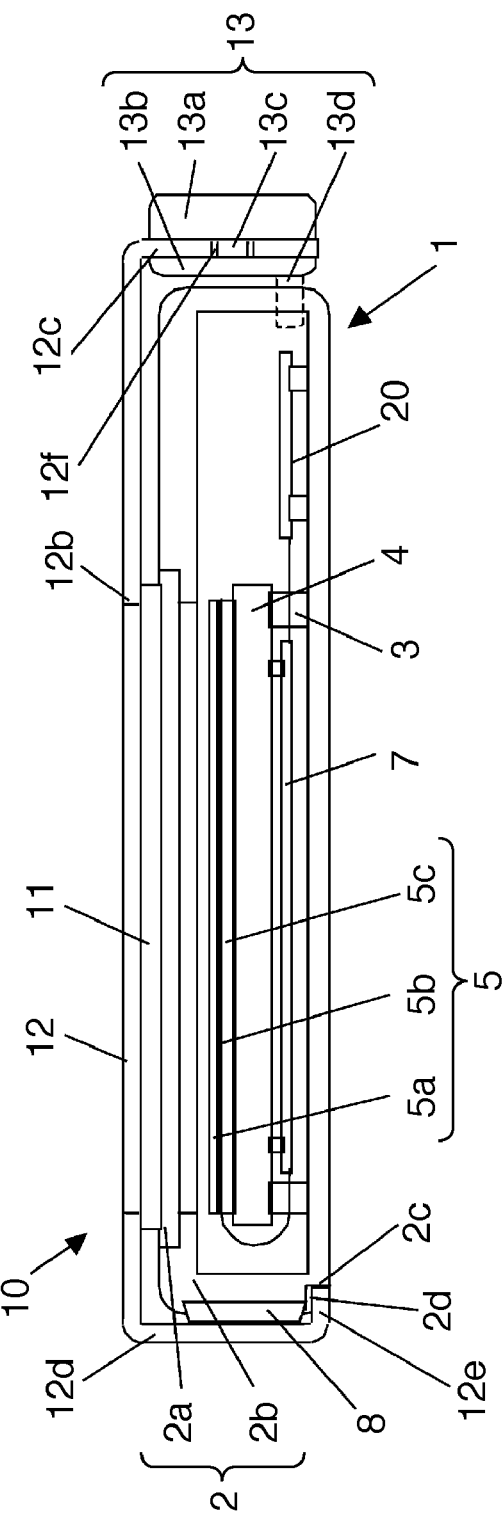

RADIATION IMAGING APPARATUS

BACKGROUND OF THE INVENTION

1. Field of the Invention

The present invention relates to a radiation imaging apparatus using a portable solid-state imaging device configured to allow a grid to be mounted outside the housing.

2. Description of the Related Art

Conventionally, apparatuses which obtain radiographic images of objects by irradiating the objects with radiation and detecting the intensity distributions of radiation transmitted through the objects have been widely and generally used in the fields of industrial nondestructive testing and medical diagnosis. As a general method for such radiography, a film/screen method using radiation is available. This is the method of performing radiography by using a combination of a photosensitive film and a fluorescent having sensitivity to radiation.

In this method, rare-earth fluorescent sheets which emit light upon application of radiation are held in tight contact with the two surfaces of a photosensitive film. The fluorescent converts radiation transmitted through an object into visible light. The method then develops, by chemical treatment, the latent image formed on the photosensitive film by making it capture this visible light, thereby visualizing the image.

The recent advances in digital technology have popularized the scheme of obtaining high-quality radiographic images by converting radiographic images into electrical signals, performing image processing for the obtained electrical signals, and then reproducing the resultant information as visible images on a CRT or the like. As such a method, there has been proposed a radiographic image recording/reproduction system which temporarily stores a transmission image of radiation as a latent image in a fluorescent, photoelectrically reads out the latent image by irradiating the fluorescent with exciting light such as a laser beam, and then outputs the readout image as a visible image. In addition, with the recent advances in semiconductor process technology, there has been developed an apparatus for capturing a radiographic image in the same manner as described above by using a semiconductor sensor.

These systems have very wide dynamic ranges as compared with conventional radiographic systems using photosensitive films, and can obtain radiographic images which are robust against the influences of variations in the amount of radiation exposure. At the same time, unlike the conventional photosensitive film scheme, this method need not perform any chemical treatment and can instantly obtain an output image.

FIG. 7 is a view showing the arrangement of a radiation imaging system using the above semiconductor sensor. A radiation imaging apparatus 103 mounted on a radiographic stand 106 includes a solid-state imaging device 104 having a detection surface on which a plurality of photoelectric conversion elements are two-dimensionally arranged.

A radiation generator (X-ray tube) 101 emits radiation to irradiate an object 102. The solid-state imaging device 104 then images the radiation transmitted through the object 102, and converts it into visible light through the fluorescent. A control unit 107 reads out the electrical signal output from the solid-state imaging device 104, performs digital image processing for the signal, and then displays the resultant information as a radiographic image of the object 102 on a monitor 108.

The radiation imaging apparatus 103 as an imaging unit incorporates an anti-scatter grid (to be referred to as a grid hereinafter) 105. The grid is designed to remove scattered X-rays generated inside the object (e.g., a human body) 102 upon X-ray irradiation, and is used to improve the contrast of an X-ray image. This apparatus performs radiography with the grid 105 being disposed between the X-ray tube 101 and a detector such as a film. Such grids are defined as JIS Z 4910 anti-scatter grids, which will be briefly described below.

FIG. 8 is a schematic sectional view of the grid described above. X-rays are applied from a direction A on the left side of FIG. 8. The grid is formed by alternately stacking foils 201 made of a material having a high X-ray absorptance and intermediate materials 202 having a low X-ray absorptance. In general, lead is used for the foils 201 having a high absorptance, and aluminum, paper, wood, synthetic resin, carbon fiber reinforced resin, or the like is used for the intermediate materials 202 having a low X-ray absorptance. The outer surface of this multilayered structure is covered by, for example, an aluminum or carbon fiber reinforced resin cover.

In many cases, the above grid is a focused grid including a foil represented by a foil 201a which is located at a central portion immediately below the X-ray source and is perpendicular to the cover and foils 201b which gradually tilt in the direction of the light source toward the fringes. When a focused grid is to be used, it is necessary to perform radiography upon adjusting the distance between the grid and the light source and their centers. A grid without any tilting of foils is also available, which is called a parallel grid. Such grids differ in the property of attenuating transmitted X-rays depending on the density or geometrical shape of foils. A grid with optimal specifications is selected in accordance with radiography. In particular, the solid-state imaging device 104 described above is generally selected so as to prevent the pixel size from interfering with the intervals between grid foils in terms of frequency.

An imaging apparatus of this type has been installed and used in a radiation room. Recently, a portable imaging apparatus (also called an electronic cassette) has also been provided to allow quicker radiography of regions in a wider range.

Such an electronic cassette is required to be low in profile and lightweight and have high mechanical strength. In cassette radiography, a person as an object may be rested on the cassette. In addition, since the electronic cassette is portable, a shock may act on the cassette if it is dropped or collides with something. As compared with conventional stationary imaging units, therefore, it is necessary to greatly improve the resistance of such electronic cassettes in terms of mechanical strength.

A cassette can be applied to various regions, and hence the grid is preferably configured to be easily attached/detached depending on a region to be radiographed. Therefore, a grid which can be mounted outside an imaging unit has been proposed as disclosed in Japanese Patent Laid-Open No. 2004-177251. This grid is mounted on a metal frame component to secure its mechanical strength.

As a grid mounted outside an imaging unit like that described above, a grid having the following characteristics has been provided. The first characteristic is that a metal frame member is mounted on the grid body to protect it in terms of mechanical strength. The second characteristic is associated with the pixel array of the imaging unit and the relative angle of the grid lattice.

Unlike film radiography, digital imaging has the merit of reducing, by image processing, streaks appearing on an image when the foils of the grid are captured on it. For this reason, the relative angle preferably falls within the computational tolerance of image processing. Therefore, in order to make the relative angle fall within the tolerance range, the grid is mounted on the imaging unit with a side wall being provided on a frame member for positional restriction for the imaging unit. In addition, some grids have a buffer member mounted on a side wall to prevent the operator from being injured if the grid is accidentally dropped or to prevent the grid from being damaged during transport.

Consider a case in which a portable X-ray imaging apparatus 111 is used to radiograph a side surface of a head portion 110 on a table 114, as shown in FIG. 9. In this case, since a distance L from the outer shape of a grid fixing frame 113 to an effective imaging area 112 of the imaging unit 111 is large, it is necessary to use a tool for applying some correction for an offset relative to an object. That is, such radiography accompanies cumbersome operation.

Studies have been focused on the imaging unit to meet the requirement for a reduction in weight. In practice, however, it is necessary to implement weight reduction, including a reduction in the weight of the grid.

SUMMARY OF THE INVENTION

The present invention provides a radiation imaging apparatus including a grid unit which makes improvements in the distance to an effective imaging area and the mass, which contradict the implementation of required relative angle restriction, the securement of mechanical strength, and protection against a shock.

According to one aspect of embodiments, the present invention relates to a radiation imaging apparatus comprising a detection unit for detecting a radiation distribution transmitted through an object, an imaging unit which includes the detection unit, and a grid for suppressing scattered light which is detachably mounted on an outside of the imaging unit, wherein the imaging unit includes a buffer member on a side surface facing a surface side which radiation strikes, the grid includes a grid body placed on the surface side which the radiation strikes, and a fixing unit for fixing the grid body to the imaging unit, and sides constituting the fixing unit include a side which does not protrude from an outer shape of the imaging unit when viewed from the surface side which the radiation strikes.

Further features of the present invention will become apparent from the following description of exemplary embodiments (with reference to the attached drawings).

BRIEF DESCRIPTION OF THE DRAWINGS

FIG. 3 is a side sectional view taken along a line A-A of the imaging unit according to the first embodiment with the grid unit being mounted on it;

FIG. 4 is a side sectional view taken along a line B-B of the imaging unit according to the first embodiment with the grid unit being mounted on it;

DESCRIPTION OF THE EMBODIMENTS

The embodiments of the present invention will be described in detail with reference to the accompanying drawings.

Figure 1:
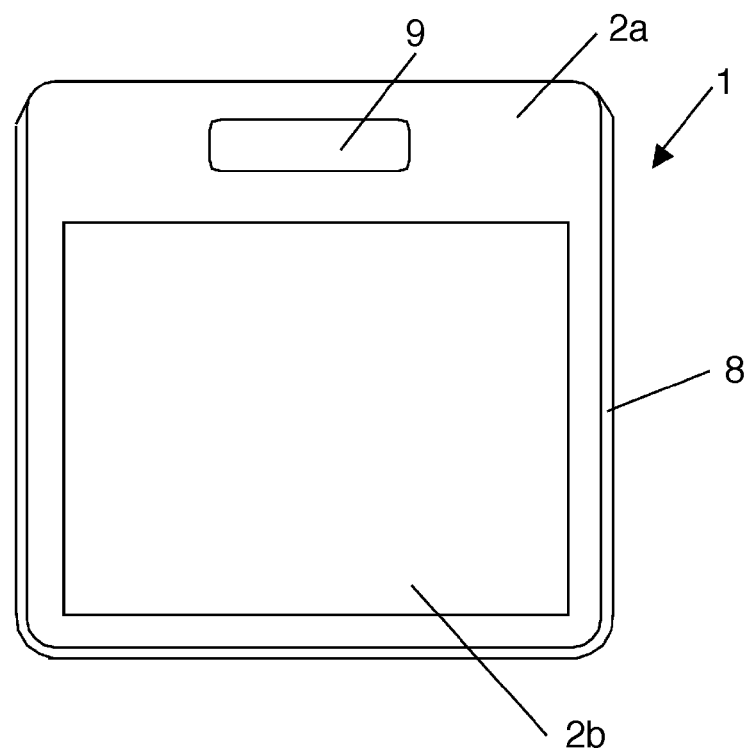
FIG. 1 is a front view of a radiation imaging unit according to the first embodiment.
Figure 2:
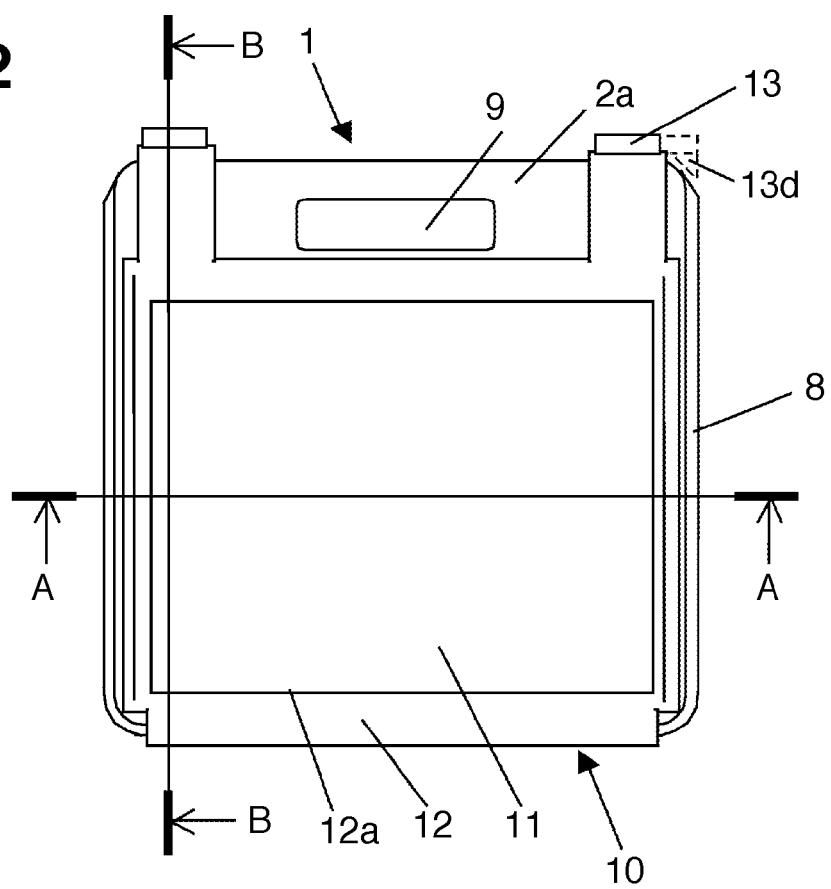
FIG. 2 is a front view showing the imaging unit according to the first embodiment when a grid unit is mounted on it.

FIGS. 1 to 4 show an X-ray imaging apparatus according to an embodiment of the present invention. FIG. 1 is a front view showing an imaging unit alone when viewed from the X-ray incident surface. FIG. 2 is a front view showing the imaging unit when a grid unit is mounted on it. Referring to FIG. 2, reference numeral 1 denotes an imaging unit; and 10, an anti-scatter grid unit. FIG. 3 is a side sectional view taken along a line A-A in FIG. 2. FIG. 4 is a side sectional view taken along a line B-B in FIG. 2.

FIG. 1 is a front view showing the radiation imaging unit 1 alone when viewed from the X-ray incident surface side. An X-ray detection unit which receives X-rays and detects a radiation distribution is rectangular. A housing lid 2b is placed on the X-ray incident surface side so as to cover an image-receiving area. The housing lid 2b is made of a material having a high X-ray transmittance. The housing lid 2b is combined with a housing body 2a to form a closed type housing 2 having a rectangular shape (almost a quadrangle).

The radiation imaging unit 1 described above is used singly as a cassette or used in combination with various gantries. Requirements for transportation in changing the state of use are that the imaging unit 1 is lightweight, and has mechanical strength sufficient to maintain functionality even if it is dropped. In addition, when the imaging unit 1 is to be used as a cassette, the unit must be made low in profile to prevent a person as an object from feeling pain even if the unit is placed under him/her, and needs to have mechanical strength high enough to allow him/her to directly rest upon it.

For this purpose, a material such as aluminum or magnesium is used for the housing body 2a to achieve a reduction in weight. In addition, to prevent accidents during transportation like those described above, the imaging unit 1 has a handle and a buffer function. The imaging unit 1 has a hole 9 as a handle which extends through part of the housing. This allows stable gripping of the imaging unit 1 during transportation. A buffer member 8 is placed around the side surfaces of the imaging unit 1 when viewed from the X-ray irradiation surface side.

The buffer member 8 is placed on the imaging unit 1 as shown in FIG. 1 because the three sides other than one side (near the handle) where the handle is formed tend to sustain damage due to collisions with other objects or due to dropping when the operator carries the unit while gripping the handle. The buffer member 8 is made of a shock absorbing material such as rubber or an elastomer, and is aimed at protecting an operator as well as other people from injury to themselves as well as at reducing the shock absorbed by the imaging unit 1.

The imaging unit 1 described above is used in combination with a detachable grid for suppressing scattered light to improve the contrast of an X-ray image by removing scattered X-rays generated inside an object (e.g., a human body) upon X-ray irradiation. Since grids having different X-ray shielding characteristics are selectively used in accordance with the region to be radiographed, the grid unit is designed to be externally attached/detached to/from the housing 2 so as to be easily attached/detached to/from the imaging unit, as shown in FIG. 2.

Referring to the side sectional view shown in FIG. 3, a metal base 4 is fixed in the housing 2 through a support portion 3, and an X-ray image detection panel 5 formed by stacking a substrate 5a, photoelectric conversion elements 5b, and a fluorescent plate 5c is placed on the base 4. As the substrate 5a, a glass plate is often used because, for example, it must not have any chemical action with a semiconductor element and needs to endure the semiconductor process temperature and have dimensional stability.

The photoelectric conversion elements 5b are formed on the substrate 5a in a two-dimensional array by a semiconductor process. The fluorescent plate 5c used is one that is formed by coating a resin plate with a metal compound fluorescent. They are integrated with each other with an adhesive. In addition, the photoelectric conversion elements 5b are connected, through a flexible circuit board 6 connected to their side surfaces, to a circuit board 7 which is placed on the lower surface of the base 4 and on which electronic parts for processing electrical signals having undergone photoelectric conversion are mounted. The circuit board 7 is connected to an external control unit (not shown) to, for example, supply power and transfer signals.

The radiation imaging unit 1 described above can perform radiography by being used in combination with an X-ray tube which emits X-rays. When the X-rays emitted by the X-ray tube positioned above the imaging unit 1 are transmitted through an object and strike the radiation imaging unit 1, the fluorescent plate 5c of the X-ray image detection panel 5 emits light. The two-dimensionally arrayed photoelectric conversion elements 5b convert the light into electrical signals, thereby obtaining a digital image. This digital image is further transferred to the external control unit. This allows the operator to observe the image on a monitor (not shown) in real time.

The grid unit 10 includes a grid body 11 and a metal frame 12. As described above, the grid body 11 has a layer structure constituted by an X-ray shield member and an intermediate material having small X-ray absorption, and hence is low in mechanical strength. The grid body 11 is therefore attached with the frame 12 as a reinforced frame which has an X-ray transmission opening portion 12a. The grid body 11 is held on the surface of the imaging unit 1 on the incident surface side in tight contact with it.

The frame 12 shown in FIG. 3 has a cross-section in a direction parallel to the side having the handle. This frame has two side portions 12b which are bent by the thickness of the grid. This shape can make the edge of the frame end portion difficult to come into contact with an object and can increase the mechanical strength of the frame 12, as compared with the simple planar shape like that denoted by reference symbol E in FIG. 3. In addition, this frame can achieve a great reduction in weight as compared with a conventional frame covering the entire side surfaces.

Furthermore, the distal ends of the bent portions 12b do not protrude outside the buffer member 8 on the side surfaces of the imaging unit. This shape allows the buffer member 8 of the imaging unit 1, which is placed outside, to receive a shock first, thus reducing the shock directly acting on the grid frame 12. Even if the grid unit 10 is attached to the imaging unit 1, the distance from the outermost shape to the effective imaging area does not change. This makes it possible to perform positioning in the same manner and eliminate the necessity to use any tool to newly correct an offset relative to an object.

A means for attaching the grid unit 10 to the imaging unit 1 will be described with reference to FIG. 4. The frame 12 is bent in an almost U shape to have bent portions 12c and 12d so as to hold, between them, the side having the handle and its opposite side. A stepped portion 2c is formed on the housing 2 so as to lock a bent portion 12e of the frame. The frame 12 is mounted on the housing 2 while a side surface wall 2d of the stepped portion 2c restricts the movement of the frame 12 in the horizontal direction (the vertical direction in FIG. 4).

On the other hand, a stepped portion is also provided on the side on the handle side so as to lock a hook 13d of a slide member 13 provided on the bent portion 12c of the frame 12. A guide member 13c is mounted on the slide member 13 so as to be slidable on guide grooves 12f formed in the bent portion 12c. Simple operation can detachably mount the grid unit 10 on the imaging unit 1.

This lock mechanism allows to safely carry the imaging unit 1 even while the grid unit 10 is mounted on it. The bent portion 12d of the frame 12 and the slide member 13 hold the imaging unit 1 between them. This structure therefore restricts the rotation of the grid unit 10 so as to make the relative angle of the grid unit 10 with respect to the imaging unit 1 fall within a predetermined angle.

Figure 5:
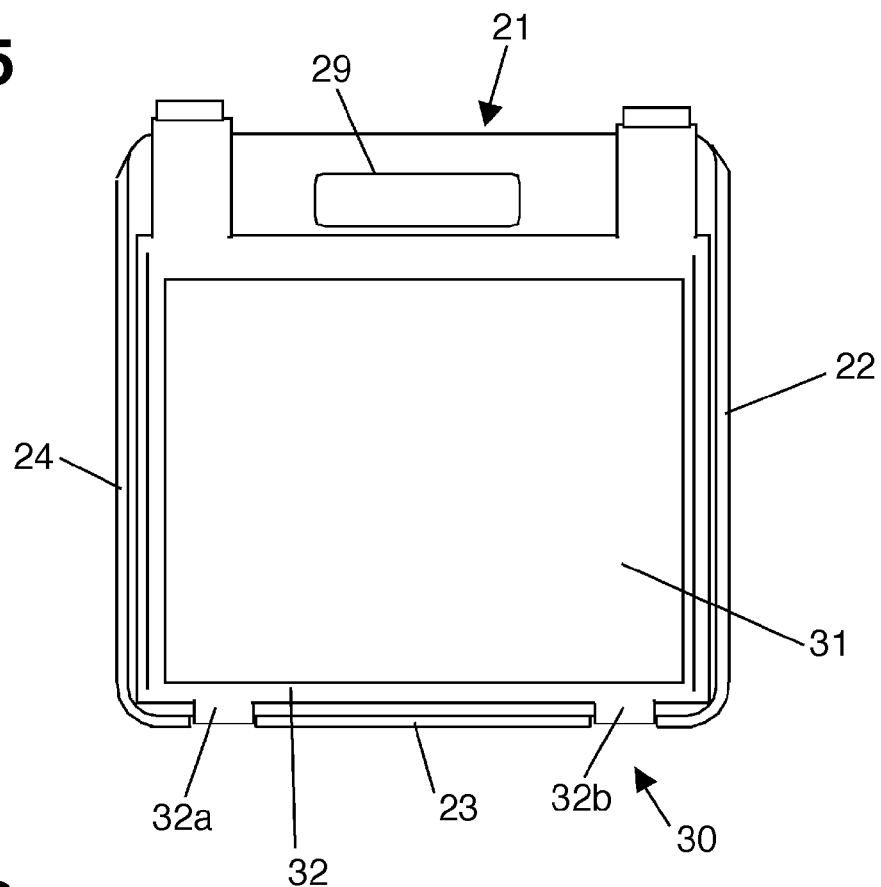
FIG. 5 is a front view showing an imaging unit according to the second embodiment when a grid unit is mounted on it.

FIG. 5 shows an X-ray imaging apparatus according to another embodiment of the present invention, which is a modification of the above embodiment. According to the above embodiment, the frame of the grid unit is formed to expose the buffer member provided on the side surfaces of the imaging unit on the two sides perpendicular to the side where the handle is formed, and the grip unit defines the outermost shape on the side on which the handle is formed and its opposite side. If an imaging area is rectangular, it is necessary to select the portrait orientation or the landscape orientation as the suitable posture of the imaging unit. If radiography is performed with the long side being the bottom, the distance from the outermost shape to the effective imaging area undesirably increases.

In order to cope with this problem, in this embodiment, a buffer member is partly notched to be divided into parts 22, 23, and 24. Bent portions 32a and 32b for locking which are provided on a frame member 32 on which a grid 31 is to be mounted are placed in the gaps between the respective parts. With this arrangement, the buffer members 22, 23, and 24 of an imaging unit 21 on the sides other than the side where a handle 29 is formed each define the outermost shape. That is, the three sides have the same effect as that described in the first embodiment. Setting the width of the bent portions 32a and 32b to reduce backlash in the gaps between the respective parts of the buffer member can manage the relative position accuracy of the grid 31 with respect to the imaging unit 21 within a predetermined range.

Figure 6:
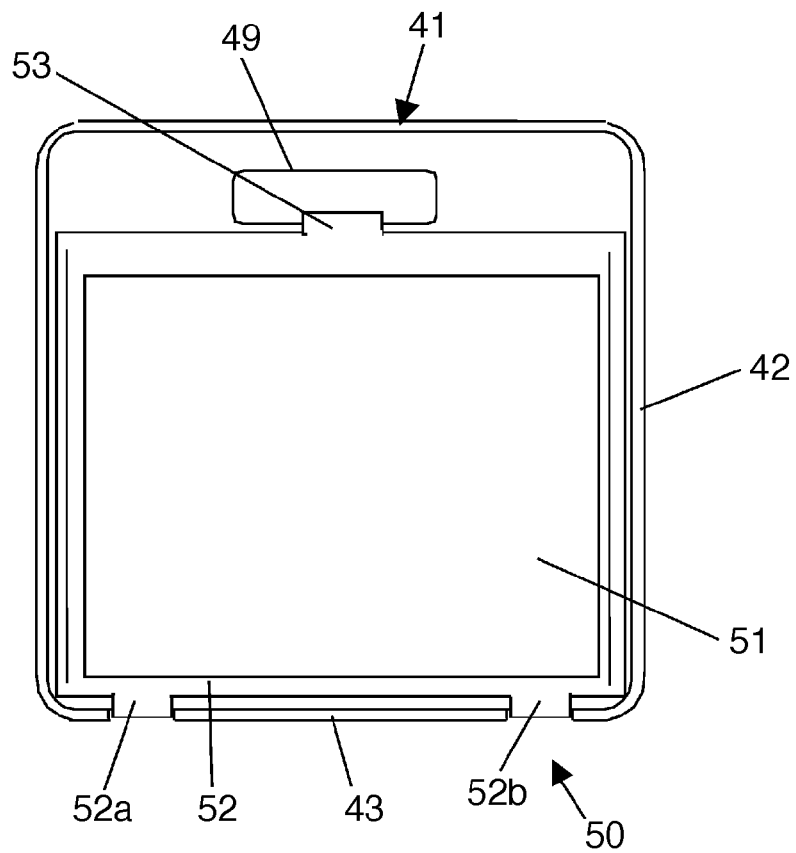
FIG. 6 is a front view showing an imaging unit according to the third embodiment when a grid unit is mounted on it.
Figure 7:
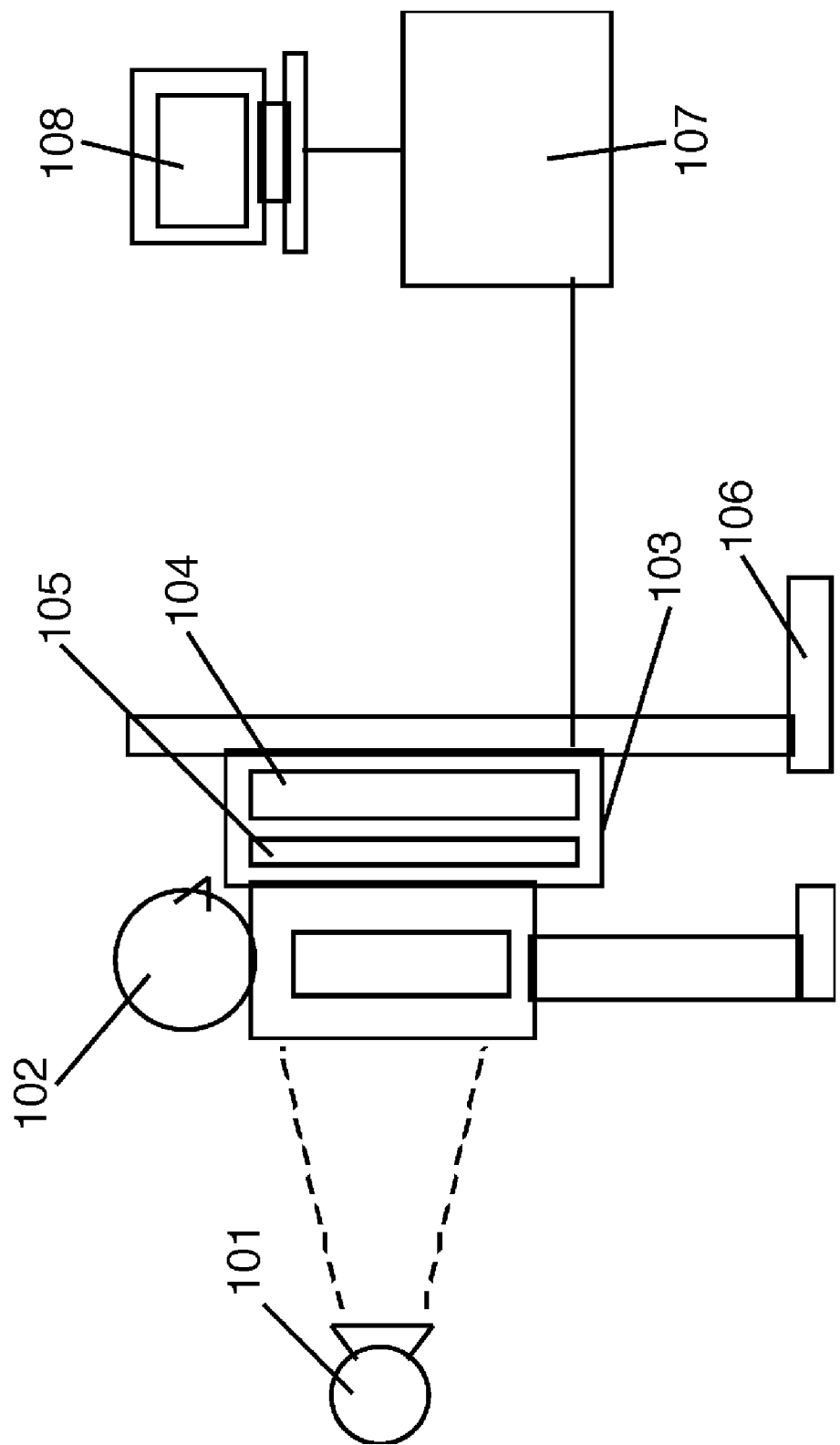
FIG. 7 is a view showing the arrangement of a conventional radiation imaging system.
Figure 8:
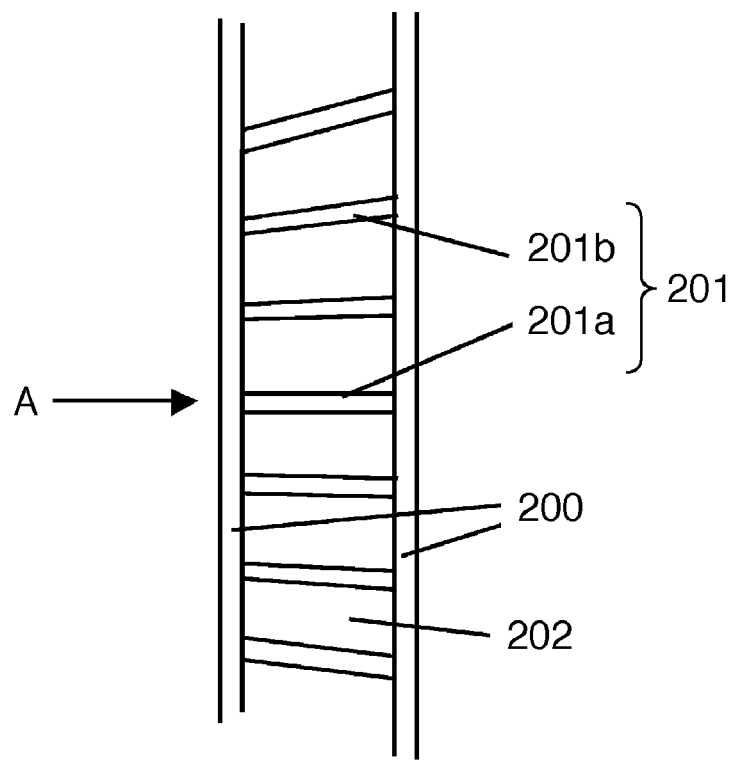
FIG. 8 is a view for explaining a grid.
Figure 9:
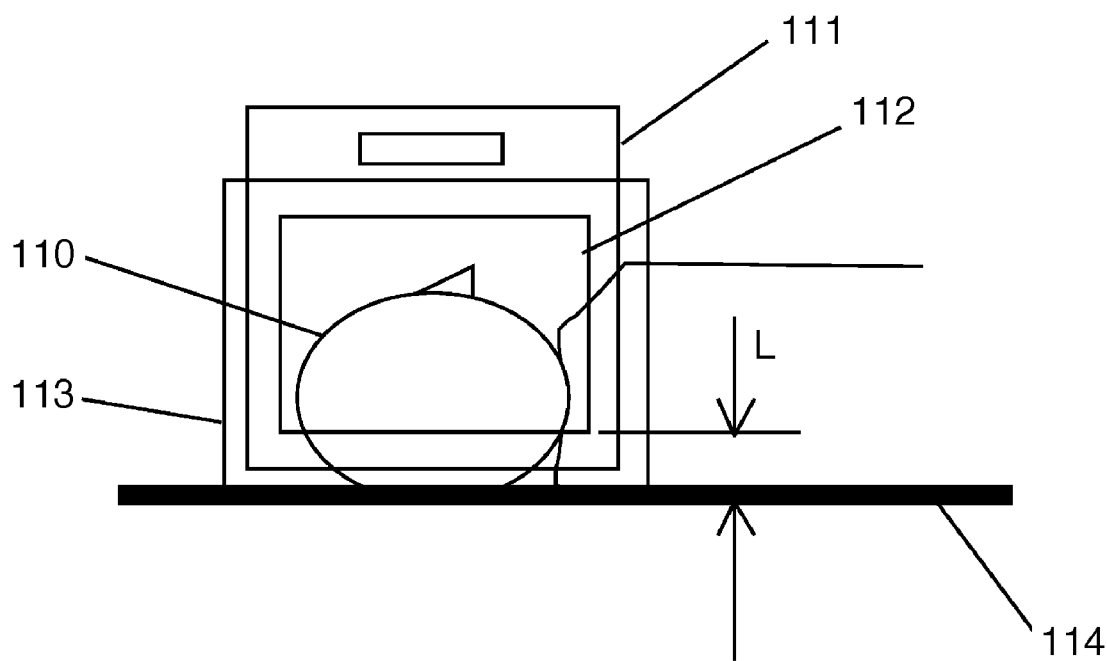
FIG. 9 is a view for explaining how a head portion is placed in radiography of a side surface of the head portion.

FIG. 6 shows an X-ray imaging apparatus according to still another embodiment of the present invention, which is a modification of the embodiment shown in FIG. 5.

In the embodiment shown in FIG. 5, the outer shape of the imaging unit defines the outermost shape at the three sides. In this embodiment, however, a grid unit is formed such that the outer shape of an imaging unit at the four sides including the side where a handle is formed defines the outermost shape. Buffer members 42 and 43 are placed on the entire side surfaces of an imaging unit 41. This arrangement allows the effect of reducing shock even when the imaging unit 41 is accidentally dropped as well as when a shock acts on the imaging unit 41 while the operator is gripping the handle and transporting the imaging unit 41. A grid unit 50 includes a lock portion 53 which is locked in a through hole 49 formed as a handle. The grid unit 50 is mounted on the imaging unit 41 by holding it with bent portions 52a and 52b and the lock portion 53.

As described above, a grid frame 52 does not completely protrude from the outer shape of the imaging unit 41 when viewed from the incident surface side. This makes it possible to maintain the same effect against a shock from the side surface direction as that obtained when the imaging unit is used singly, even in a state in which the grid unit 50 is mounted on the imaging unit.

The embodiments of the present invention have been described above. Obviously, however, the present invention is not limited to these embodiments. Various modifications and changes of the embodiments can be made within the spirit and scope of the present invention.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-090486, filed Apr. 2, 2009, which is hereby incorporated by reference herein in its entirety.

What is claimed is:

1. A radiation imaging apparatus comprising:
   a detection unit for detecting a radiation distribution transmitted through an object;
   an imaging unit which includes said detection unit; and
   a grid for suppressing scattered light which is detachably mounted on an outside of said imaging unit,
   wherein said imaging unit includes a buffer member on a side surface facing a surface side which radiation strikes,
   said grid includes a grid body placed on the surface side which the radiation strikes, and a fixing unit for fixing the grid body to said imaging unit, and
   sides constituting the fixing unit include a side which does not protrude from an outer shape of said imaging unit when viewed from the surface side which the radiation strikes.

2. The apparatus according to claim 1, wherein said imaging unit includes a handle, and
   a side of said fixing unit which is perpendicular to a side located near the handle when viewed from the surface side which the radiation strikes does not protrude from the outer shape of said imaging unit.

3. The apparatus according to claim 2, wherein a side of the buffer member of said imaging unit which is parallel to the side located near the handle when viewed from the surface side which the radiation strikes includes a notched portion, and
   the fixing unit is positioned by the notched portion at a side parallel to the side located near the handle, and the parallel side is a side which does not protrude from the outer shape of said imaging unit.

4. The apparatus according to claim 2, wherein the fixing unit includes bent portions, each having a substantially U-shaped cross-section, which hold said imaging unit therebetween, and is mounted on said imaging unit while holding, therebetween, the side including the handle of said imaging unit and an opposite side.

5. The apparatus according to claim 3, wherein the fixing unit includes a lock portion which locks to the handle and bent portions, each having a substantially U-shaped cross-section, which are arranged to hold said imaging unit therebetween at a position of the notched portion, and is mounted on said imaging unit while holding said imaging unit by the lock portion and the bent portions.

6. The apparatus according to claim 1, wherein the fixing unit of said grid has a shape which is bent toward said imaging unit on an incident surface side of said imaging unit so as to cover a gap corresponding to a thickness of the grid body between the grid body and the fixing unit, and so as not to protrude from a side surface.

* * * * *